United States Patent [19]
Tornier

[11] Patent Number: 5,702,478
[45] Date of Patent: Dec. 30, 1997

[54] ACETABULAR IMPLANT INTENDED IN PARTICULAR FOR THE ILIAC JOINT SOCKET

[75] Inventor: Alain Tornier, Saint-Ismier, France

[73] Assignee: Tornier SA, Saint-Ismier, France

[21] Appl. No.: 657,890

[22] Filed: Jun. 7, 1996

[30] Foreign Application Priority Data

Jun. 16, 1995 [FR] France ................. 95 07448

[51] Int. Cl.[6] ............................ A61F 2/34
[52] U.S. Cl. ................................ 623/22
[58] Field of Search ................... 623/22–23

[56] References Cited

U.S. PATENT DOCUMENTS

| | | |
|---|---|---|
| 3,903,549 | 9/1975 | Deyerle . |
| 3,918,102 | 11/1975 | Eichler ................. 3/1.912 |
| 5,108,448 | 4/1992 | Gautier ................ 623/22 |
| 5,163,961 | 11/1992 | Harwin . |

FOREIGN PATENT DOCUMENTS

| | | |
|---|---|---|
| 0153523 | 4/1985 | European Pat. Off. . |
| 0336884 | 11/1989 | European Pat. Off. . |
| 0430831 | 5/1991 | European Pat. Off. . |
| 0549483 | 6/1993 | European Pat. Off. . |
| 2597747 | 4/1986 | France . |
| 2617040 | 6/1987 | France . |
| 2638963 | 11/1988 | France . |
| 2676172 | 7/1991 | France . |

*Primary Examiner*—David Isabella
*Assistant Examiner*—John M. Black
*Attorney, Agent, or Firm*—Dowell & Dowell

[57] ABSTRACT

An acetabular or cotyloid implant intended in particular for the iliac joint socket, which comprises a metallic cage and an insert made of plastic material. The cage, which is spherical in form, is constituted by a metal frame of slight thickness composed of a network of narrow blades defining therebetween large free spaces, while the insert made of plastic material is solidly assembled with the cage.

17 Claims, 3 Drawing Sheets

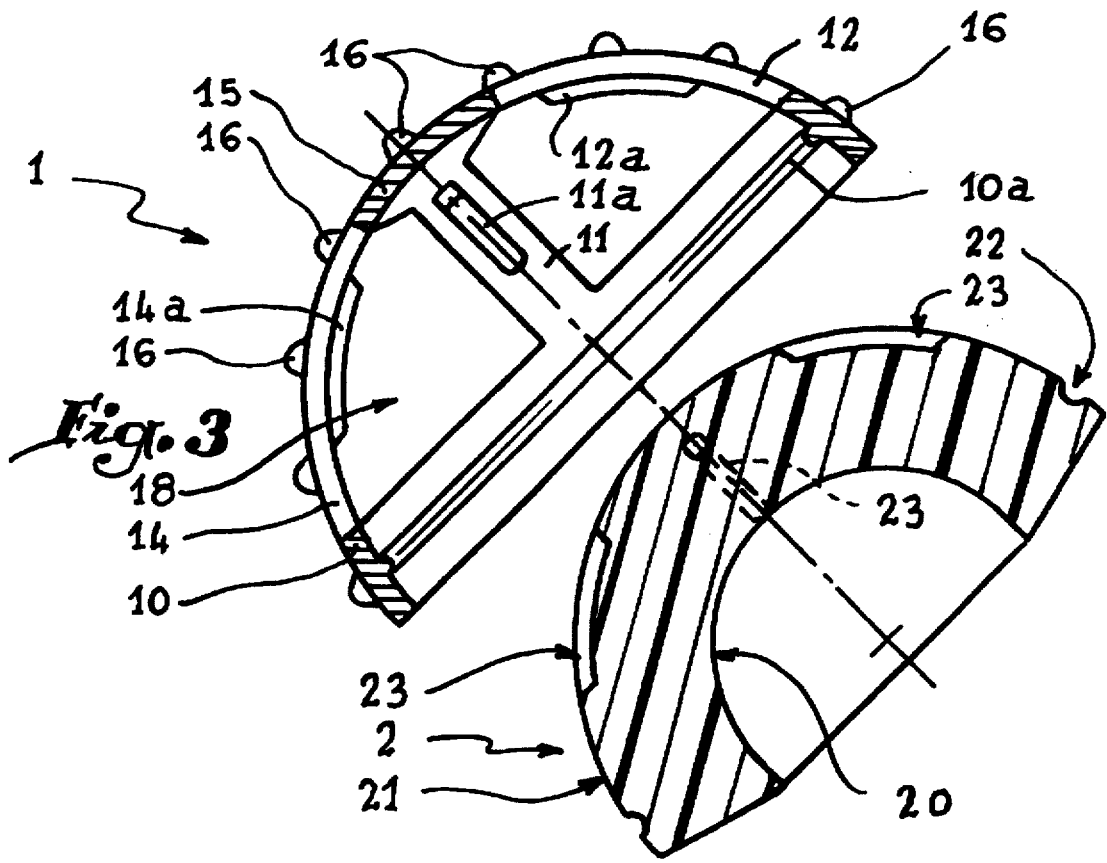
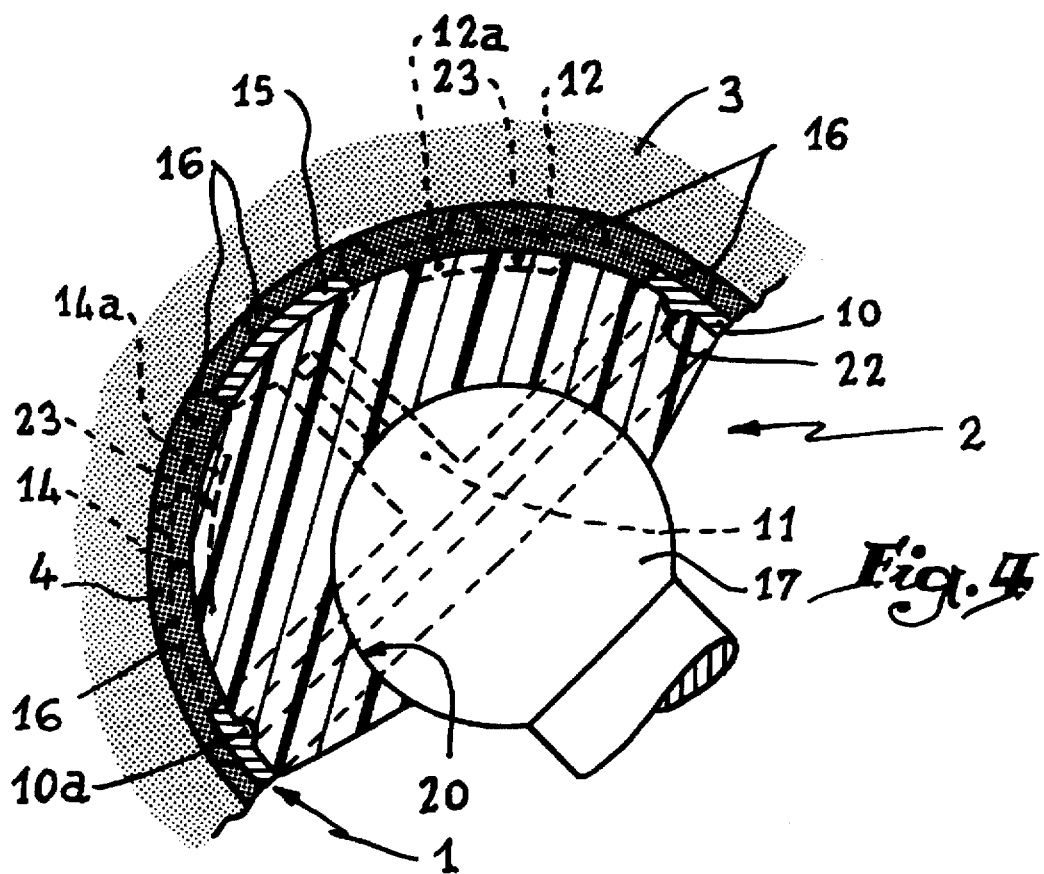

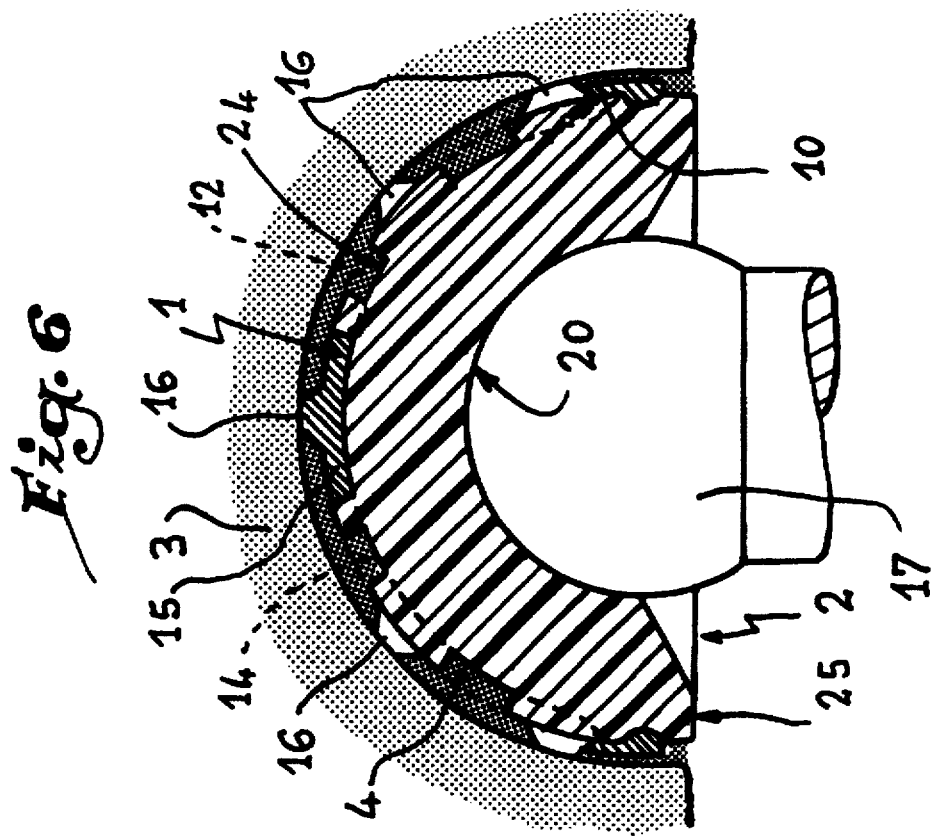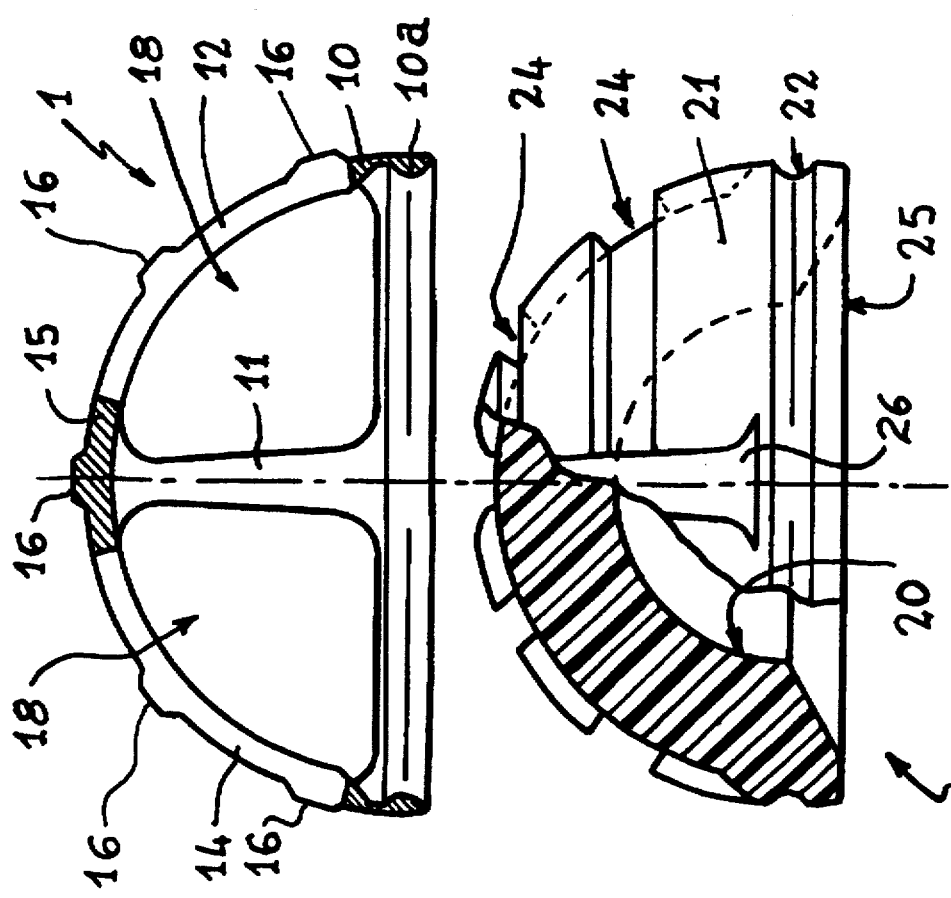

ACETABULAR IMPLANT INTENDED IN PARTICULAR FOR THE ILIAC JOINT SOCKET

FIELD OF THE INVENTION

The present invention relates to an acetabular or cotyloid implant adapted to be placed in a damaged joint socket, particularly the acetabulum of a patient, and in particular in cooperating with the head of a femoral prosthesis, the assembly constituting a total hip prosthesis.

HISTORY OF THE RELATED ART

Acetabular implants made entirely of plastic material are known, intended to cooperate with a natural or artificial femoral head in a hip arthroplasty. Such implants are positioned using a cement which bonds them to the damaged joint socket.

Acetabular implants are also known, composed of two parts, viz. a metallic cage assembled on a patient's acetabulum and which comprises a hollow containing an insert made of plastic material. The metallic cage or envelope may be positioned with the aid of an acrylic cement or directly without cement for example by screwing in the iliac bone, as described in Applicants' FR-2 638 963.

Acetabulum implants made entirely of plastics material present a modulus of elasticity close to that of the bone in which they are implanted and similar to that of the acrylic cement intended for bonding them, with the result that the implant and the bone which receives it form a composite assembly which is homogeneous from the standpoint of elasticity.

However, such implants have drawbacks concerning possible contacts of the plastics material with the bone tissue, for example when the cement is not distributed equally over the outer face of the implant. Acquired clinical experience demonstrates that such contact may, in certain cases, bring about negative reactions of the receiving medium.

The elasticity of the two-part acetabulum implants as indicated herein above is reduced to that of their metallic envelope which is much more rigid than the receiving bone. Moreover, as the modulus of elasticity of the metal is very different from that of the plastic material, the acrylic cement and the bone, the assembly is heterogeneous from that point of view. On the contrary, contact between the metal and the bone tissue raises no problem, on condition that it is suitably chosen, as is well known in practice.

It is an object of the improvements according to the present invention to overcome the drawbacks of the one-part implants made of plastics material and of those made in two parts incorporating a solid outer part, and to allow an implant to be produced which comprises an outer cage and an insert made of plastics material, which responds better than heretofore to the desiderata of the art.

SUMMARY OF THE INVENTION

To that end, the acetabular or cotyloid implant according to the invention is characterized in that its cage is constituted by a metallic frame of slight thickness composed of a narrow and circular blade forming a belt from which issue curved blades constituting branches converging towards a cap of the cage and which define large free spaces. Protuberances are disposed on the outer faces of the belt and branches and are the sole metallic contact with the bone. And insert of plastic material is assembled on said cage before the implant is sealed in the bone socket so that said insert is retained in all its axial directions with respect to said cage so that its outer face adheres directly via large free spaces of said cage to the layer of cement deposited in the bone socket.

To avoid any rotation of the insert with respect to the cage, the inner face of at least one convergent blade of the cage comprises a rib cooperating with a groove of meridian orientation made in the outer wall of the implant.

BRIEF DESCRIPTION OF THE DRAWINGS

The invention will be more readily understood on reading the following description with reference to the accompanying drawings, in which:

FIG. 3 is an exploded view in section of a variant of the implant of FIG. 4.

FIG. 4 is a view similar to that of FIG. 2, but relative to the implant of FIG. 3.

FIGS. 5 and 6 are views similar to those of FIGS. 3 and 4 but illustrating a further variant of the implant according to the invention.

DESCRIPTION OF PREFERRED EMBODIMENT

Figure 1:
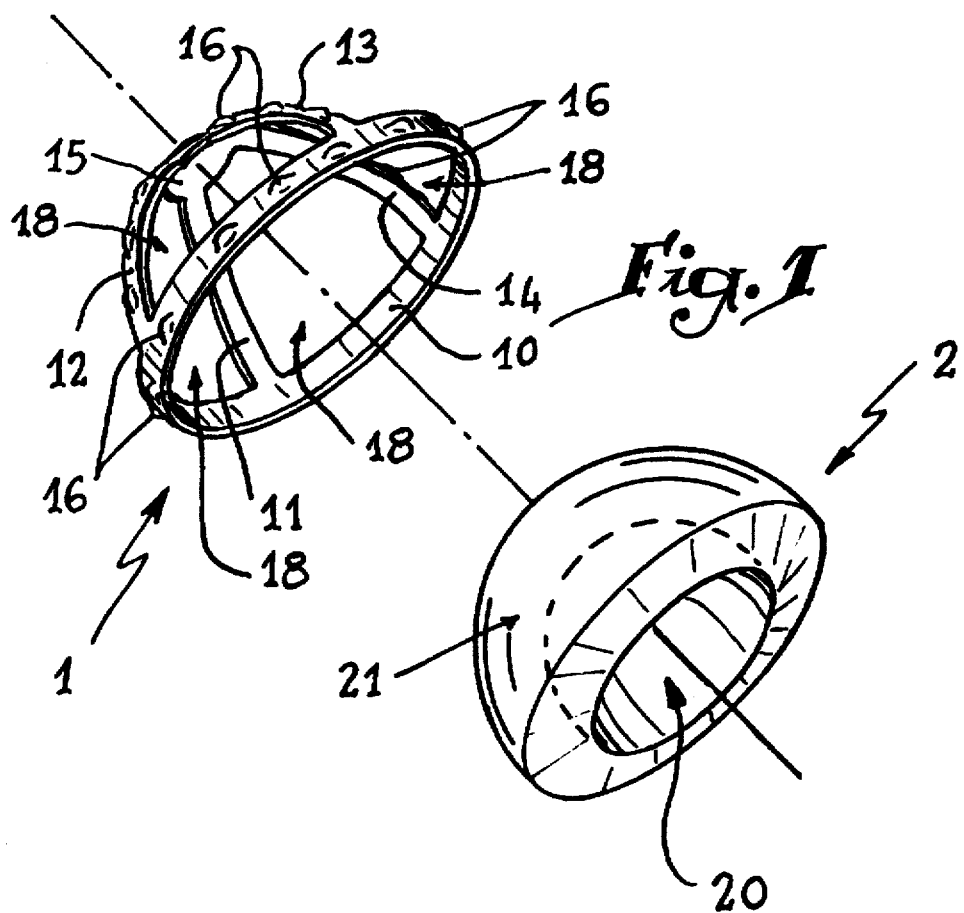
FIG. 1 is an exploded view in perspective showing the two elements of an implant according to the invention.

Referring now to the drawings, the acetabular or cotyloid implant illustrated in FIG. 1 comprises two elements, viz. a cage 1 and an insert 2.

The cage 1 which is preferably generally semi-spherical in shape is constituted by a metal reinforcement of reduced thickness composed of a network of narrow blades. This network essentially comprises a circular blade or belt 10 from which issue curved branches 11, 12, 13, 14 which converge towards a polar cap 15 of the cage and define therebetween wide openings or free spaces 18. In other words, the branches are oriented along meridians of the cage.

It is observed that the outer faces of the belt 10 and the branches 11, 12, 13, 14 comprise protuberances 16 projecting towards the outside with respect to the faces.

The insert 2 is made of a plastics material such as polyethylene, its outer shape taking the form of a portion of sphere whose diameter is provided to fit in the cage 1. The insert 2 has, in known manner, a cavity 20 made therein, in the form of a portion of sphere, as will be more readily explained hereinbelow. The outer face 21 of the insert 2 is treated so that it is adapted to adhere correctly to the surgical cement usually used. It is observed that the cage 1 and the insert 2 are truncated portions of a sphere.

Figure 2:
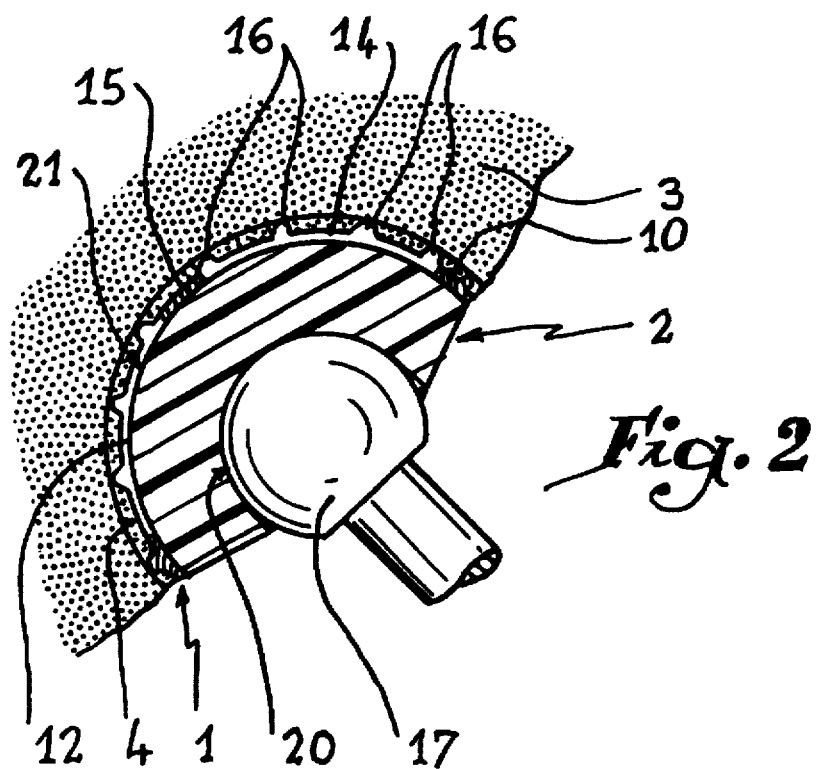
FIG. 2 illustrates in section the implant according to the invention positioned in a patient's damaged iliac joint socket.

FIG. 2 shows the implant of FIG. 1 assembled in a bone socket 3. To make this assembly, the bone socket 3 is milled so that it takes a spherical shape corresponding to the outer shape of the cage 1. After deposit of a layer of cement 4 in the bone socket thus prepared, the acetabular prosthesis, composed of the cage 1 assembled on the insert 2, is introduced until contact of the protuberances 16 with the bone. It will be noted that the openings or free spaces 18 of the cage 1 allow the outer surface 21 to be in direct contact with the layer of cement 4 deposited in the bottom of the bone socket 3. In addition, the protuberances 16 make it possible to prevent any contact of the polyethylene with the bone socket 3.

Moreover, the layer of cement 4 is also provided to cover the branches 11, 12, 13, 14 of cage 1 since only the protuberances 16 are in contact with the bottom of the bone socket 3.

In a preferred embodiment of the foregoing arrangement, and as illustrated in FIG. 3, the inner face of the belt 10 is provided with an annular bead 10a consequently projecting inwardly. The insert 2 is provided with a peripheral groove 22, receiving by elastic deformation the belt 10 and more particularly the bead 10a to allow the cage 1 to be retained on the insert 2.

As such a fixation does not prevent rotation of the implant 2 about the polar axis of the cage 1, there is advantageously provided on the inner face of at least one branch 12 of the cage 1, a groove 12a longitudinal with respect to this branch and which is intended to cooperate with a groove of meridian orientation referenced 23, made on the outer face 21 of the implant 2. In a preferred embodiment, the four branches 11, 12, 13 and 14 have on their inner faces a groove 11a, 12a, 13a, 14a.

Socket 20 of the implant 2 receives, in conventional manner, the ball joint 17 of a femoral prosthesis.

FIGS. 5 and 6 show a variant of the acetabular implant 1. For clarity and concision, the elements illustrated in FIGS. 5 and 6 which are identical to those shown in FIGS. 1 to 4, have the same references, while the elements which are different have new references.

For example, cage 1 essentially comprises a circular blade or belt 10 from which issue curved branches 11, 12, 13, 14 which converge towards a polar cap 15 of the cage. The belt 10 and the branches 11, 12, 13, 14 define wide openings or free spaces 18. Similarly, the outer faces of the belt 10 and of the branches 11, 12, 13 and 14 comprise protuberances 16 projecting outwardly with respect to said faces.

It will be noted that the inner face of the belt 10 is provided with an annular bead 10a consequently projecting inwardly.

It is ascertained that branches 11, 12, 13 and 14 have a conical profile tapering so that the widest base is provided at the connection of each branch with the belt 10.

Under these conditions, opposite the widest base, each branch at the connection with the polar cap 15, is of a narrow profile.

The polyethylene insert 2 comprises on its outer face 21 a series of concentric slots 24 disposed parallel to the base 25 of the insert. Near the base 25, the insert 2 is provided with a peripheral groove 22 parallel to the slots 24 and receiving by elastic deformation the bead 10a of the belt 10 to retain the cage 1 on the insert 2.

The latter comprises meridian grooves 26 perpendicular to the slots 24 and directed towards the center of the insert. The grooves 26 are four in number, regularly distributed over the periphery of the insert 2. The grooves 26 have the same profile as that provided for the branches 11, 12, 13 and 14 of the cage 1. The grooves 26 communicating at the top of the insert to form a cavity, not referenced, which is intended to receive the polar cap 15 of the cage 1. On the contrary, it will be noted that the grooves 26 do not communicate with the peripheral bead 22 in order to allow a better retention of the cage 1 on the insert 2.

In addition, the cage 1 is assembled on the insert 2 in-works and by force, so that the cage 1 cannot be separated from the insert 2. During assembly of cage 1 on insert 2, it will be noted that the branches 11, 12, 13 and 14 cooperate with the corresponding meridian grooves 26 in order to prevent any rotation of the cage 1 about the polar axis of the insert 2.

It will be noted that the depth of grooves 26 is similar to that of slots 24.

The depth of grooves. 26 is determined as a function of the thickness of the branches 11, 12, 13, 14 of the cage 1. In fact, the branches 11, 12, 13, 14 are completely contained inside the grooves 26 in order to allow only the protuberances 16 provided on the outer faces of the belt 10 and of the branches, to project outwardly of the implant 1.

The protuberances 16 make it possible, after deposit of a layer of cement 4 in the bone socket 3, to be the only metallic elements in contact with the bone, while the layer of cement 4 penetrates in the slots 24 of the insert 2 via wide free spaces 18 to constitute the seal of the implant 1. The protuberances 16 are also provided to prevent any contact of the polyethylene insert 2 with the bone socket 3.

What is claimed is:

1. An acetabular implant for implantation in a damaged natural joint socket comprising, a hollow cage defined by a circular base and struts extending outwardly from said base and converging at a cap opposite from said base, said base and struts being strips of metal which are spaced apart to form large free spaces therebetween, said cage having projecting protuberances disposed on an outer surface thereof to provide sole metallic contact between the implant and bone, and a plastic insert having an outer surface configured to be inserted within said cage, said insert having a partial spherical recess formed therein for receipt of a complimentary spherical ball joint, said circular base of said cage having an inner surface including a bead projecting therefrom of a size and configuration to elastically snap fit and engage within a peripheral groove formed in said outer surface of said insert, wherein at least one of said struts includes a protruding rib extending from an inner surface thereof, said rib being engageable within a groove extending in a meridian orientation in said outer surface of said insert to thereby prevent rotation of said insert with repect to said cage when said insert is assembled to said cage prior to insertion of the implant into the natural joint socket such that said outer surface of said insert not covered by said struts adheres to a layer of cement deposited in the natural joint socket.

2. The implant of claim 1 wherein said struts are of a tapering profile having a wider portion adjacent said base of said cage and a narrower portion adjacent said cap of said cage.

3. The implant of claim 1 wherein said insert includes a base, and a plurality of concentric slots formed in said outer surface of said insert and generally parallel to said base of said insert.

4. The implant of claim 3 wherein said outer surface of said insert includes a plurality of meridian grooves extending generally perpendicularly with respect to said concentric slots, and said struts of said cage being receivable within said meridian grooves to thereby prevent rotation of said cage relative to said insert.

5. The implant of claim 4 wherein said meridian grooves are of a depth which is determined as a function of a thickness dimension of said struts so that said struts are seated within said meridian grooves so as to not project outwardly beyond said outer surface of said insert.

6. The implant of claim 5 in which each of said struts includes a plurality of said projecting protuberances which extend outwardly with respect to said meridian grooves.

7. The implant of claim 6 wherein each of said meridian grooves has a profile identical to a profile of each of said struts.

8. The implant of claim 1 in which said insert includes a base and an opposite top portion, meridian grooves extending generally perpendicularly with respect to said base and toward said top portion, said meridian grooves being of a size to cooperatively receive said struts therein to thereby prevent rotation of said insert relative to said cage.

9. The implant of claim 8 wherein said meridian grooves have a depth which is determined as a function of a thickness of said struts to thereby allow said struts to be seated within said meridian grooves so as not to extend outwardly beyond said outer surface of said insert.

10. An acetabular implant for implantation in a damaged natural joint socket comprising, a hollow cage defined by a circular base and struts extending outwardly from said base converging at a cap opposite from said base, said base and struts being strips of metal which are spaced apart to form large free spaces therebetween, said cage having projecting protuberances disposed on an outer surface thereof to provide sole metallic contact between the implant and bone, and a plastic insert having an outer surface configured to be inserted within said cage, said insert having a partial spherical recess formed therein for receipt of a complimentary spherical ball joint, said insert having a base and a top portion spaced from said base, meridian grooves formed in said outer surface of said insert and extending generally perpendicularly with respect to said base to said top portion of said insert, said meridian grooves being of a configuration to cooperatively receive said struts therein, wherein said insert is assembled to said cage prior to insertion of the implant into the natural joint socket such that said outer surface of said insert not covered by said struts adheres to a layer of cement deposited in the natural joint socket.

11. The implant of claim 10 wherein said meridian grooves have a depth which is determined as a function of a thickness of said struts to thereby allow said struts to be seated within said meridian grooves so as not to extend outwardly with respect to said outer surface of said insert.

12. The implant of claim 11 wherein each of said meridian grooves has a profile identical to a profile of each of said struts.

13. The implant of claim 12 wherein said circular base of said cage includes an inner surface including a continuous bead projecting therefrom of a size and configuration to elastically snap-fit and engage within a peripheral groove formed in said outer surface of said insert.

14. An acetabular implant for implantation in a damaged natural joint socket comprising, a hollow cage defined by a circular base and struts extending outwardly from said base converging at a cap opposite from said base, said base and struts being strips of metal which are spaced apart to form large free spaces therebetween, said cage having projecting protuberances disposed on an outer surface thereof to provide sole metallic contact between the implant and bone, and a plastic insert having an outer surface configured to be inserted within said cage, said insert having a partial spherical recess formed therein for receipt of a complimentary spherical ball joint, each of said struts having a tapering profile being wider adjacent said base and narrower adjacent said cap, wherein said insert is assembled to said cage prior to insertion of the implant into the joint socket such that said outer surface of said insert not covered by said struts adheres to a layer of cement deposited in the natural joint socket.

15. The implant of claim 14 in which said insert includes a base and an opposite top portion, meridian grooves extending generally perpendicularly with respect to said base and toward said top portion of said insert, said meridian grooves being of a size to cooperatively receive said struts therein to thereby prevent rotation of said insert relative to said cage.

16. The implant of claim 14 wherein said meridian grooves have a depth which is determined as a function of a thickness of said struts to thereby allow said struts to be seated within said meridian grooves so as not to extend outwardly with respect to said outer surface of said insert.

17. The implant of claim 16 wherein said circular base of said cage includes an inner surface including a continuous bead projecting therefrom of a size and configuration to elastically snap-fit and engage within a peripheral groove formed in said outer surface of said insert.

* * * * *